United States Patent
Steppe

(10) Patent No.: US 7,331,462 B2
(45) Date of Patent: Feb. 19, 2008

(54) KIT MANAGEMENT SYSTEM

(75) Inventor: Dennis L. Steppe, Corona, CA (US)

(73) Assignee: Alcon, Inc., Hunenberg (CH)

( * ) Notice: Subject to any disclaimer, the term of this patent is extended or adjusted under 35 U.S.C. 154(b) by 496 days.

(21) Appl. No.: 10/973,630

(22) Filed: Oct. 26, 2004

(65) Prior Publication Data

US 2006/0086634 A1    Apr. 27, 2006

(51) Int. Cl.
*A61B 19/02*    (2006.01)
*B65D 69/00*    (2006.01)

(52) U.S. Cl. ............ 206/570; 206/438; 206/370; 206/564

(58) Field of Classification Search ........... 206/570, 206/523, 438, 363, 370, 572, 461, 471, 557, 206/564; D24/128; 604/412; 248/51
See application file for complete search history.

(56) References Cited

U.S. PATENT DOCUMENTS

| | | | | |
|---|---|---|---|---|
| 3,696,920 A | * | 10/1972 | Lahay | 206/370 |
| 4,971,271 A | * | 11/1990 | Sularz | 248/68.1 |
| 5,226,892 A | * | 7/1993 | Boswell | 604/180 |
| 5,350,357 A | * | 9/1994 | Kamen et al. | 604/29 |
| 5,464,025 A | | 11/1995 | Charles et al. | |
| 6,012,586 A | * | 1/2000 | Misra | 206/571 |
| 6,632,189 B1 | * | 10/2003 | Fallen et al. | 206/363 |
| 2003/0055387 A1 | | 3/2003 | Sutton et al. | |

OTHER PUBLICATIONS

English language abstract for JP 2002200096, 2002, 1 page.

* cited by examiner

*Primary Examiner*—J. Gregory Pickett
(74) *Attorney, Agent, or Firm*—W. David Lee

(57) ABSTRACT

A kit management system for use in microsurgery is disclosed. The kit management system includes a plurality of tubing, surgical instruments, connectors, an instrument tray, a connector tray, and a tubing organizer. A tubing organizer for removably receiving and holding a plurality of tubing in a spaced relationship during microsurgery is also disclosed.

12 Claims, 8 Drawing Sheets

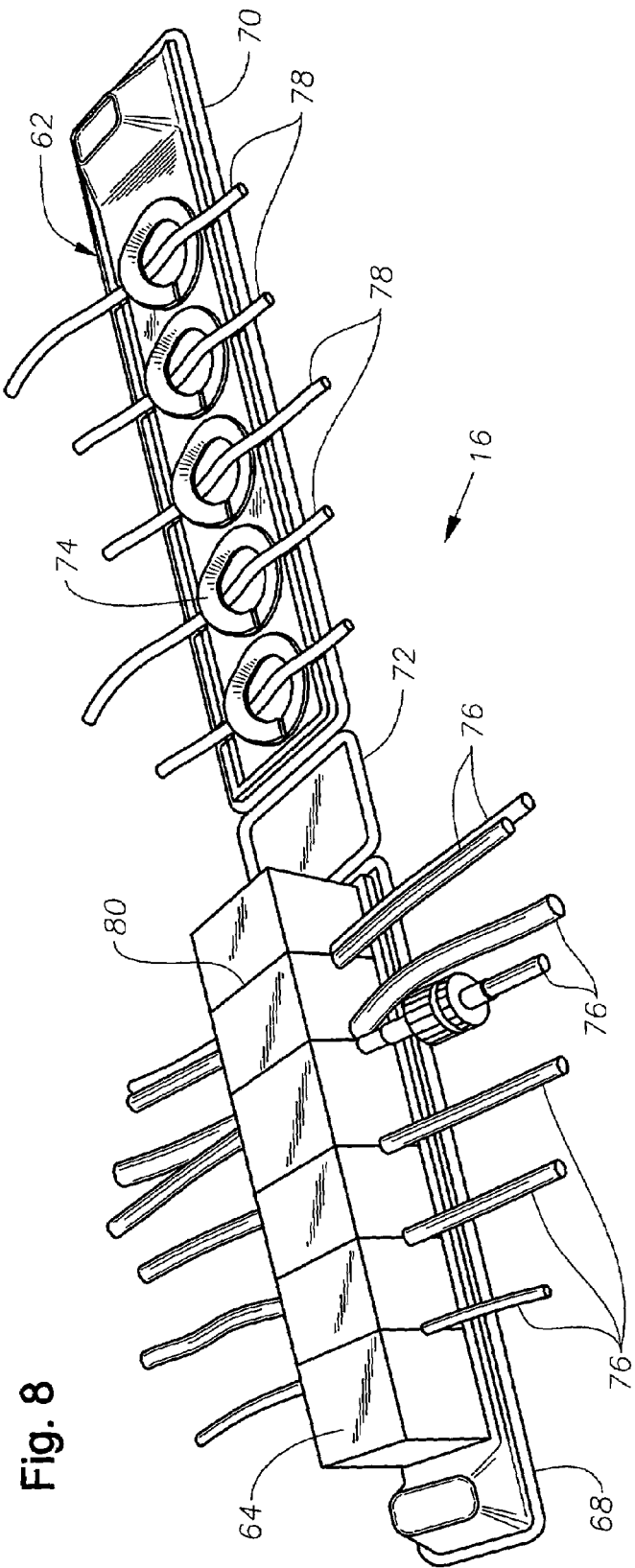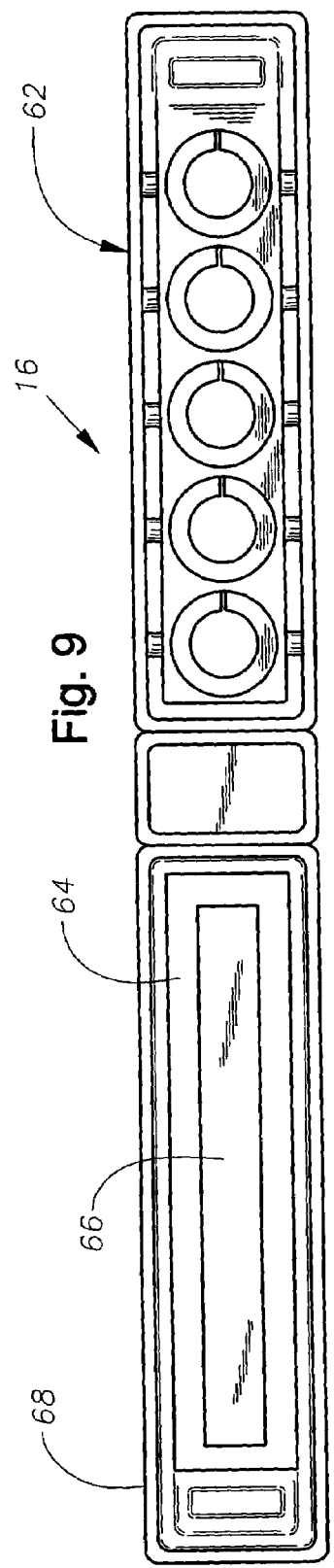

KIT MANAGEMENT SYSTEM

FIELD OF THE INVENTION

The present invention generally pertains to microsurgery and more particularly to a kit management system for use during ophthalmic surgery.

DESCRIPTION OF THE RELATED ART

A variety of surgical systems are used in ophthalmic surgery. For example, in posterior segment (vitrectomy) surgery, such systems include a surgical console, accessories (e.g. footswitch, reusable handpieces), and various consumables. The consumables are provided sterile in kits (packs) or as separately packaged items (standalones). Many of the pack consumable items or standalone consumable items consist of tubing sets or cables that connect to the console and provide a pathway from the console in the non-sterile field to a surgical handpiece or other device that is used in and remains in the sterile field. Traditionally, each tubing set or cable in the pack or standalone is separately coiled and banded.

Two persons are required to prepare the surgical system for use. One is the scrub (or sterile) nurse and the other is the circulating (or non-sterile) nurse. The scrub nurse is fully gowned and gloved and works in the sterile field, while the circulating nurse is not gowned or gloved and works in the non-sterile field. The scrub nurse must remain in the sterile field and is not allowed to contact the non-sterile field, while the circulating nurse must remain in the non-sterile field and is not allowed to contact the sterile field. Together, the scrub and circulating nurse work together in aseptically transferring sterile items from the sterile field to the non-sterile field and visa versa.

Among various duties, the scrub nurse assembles sterile items in the sterile field while the circulating nurse connects the sterile tubing set and cable connectors transferred from the sterile field to the console. Since each tubing set or cable is individually coiled and banded, the scrub nurse must locate and unband each coil, locate the appropriate end for transfer to the console, and aseptically transfer the proper end to the circulating nurse. The circulating nurse must then aseptically accept the connector end from the scrub nurse and locate the correct mating connector on the console before making the connector/console connection.

In posterior segment surgery, a number of surgical devices are characteristically required to complete the surgical procedure. These items typically consist of a fiber optic illuminator cable, an airline, a posterior infusion tubing set, vitrectomy probe tubing set, a general aspiration tubing set, an anterior irrigation tubing set, an ultrasonic handpiece, intraocular scissors, a membrane peeler cutter, a viscous fluid injector, and cautery forceps. Many of these items are provided sterile in packs or standalones. By way of example, a typical set-up using a surgical console and the above items will be briefly described.

The fiber optic illuminator cable, posterior infusion tubing set, vitrectomy probe tubing set, general aspiration tubing set, and anterior irrigation tubing set are all part of one pack. The airline and viscous fluid injector are provided as separate standalone consumables. The remaining items are reusable items that are cleaned, wrapped, and sterilized prior to the beginning of the surgical procedure. The circulating nurse first aseptically transfers each of the items to the sterile field. The scrub nurse then opens each item, uncoils the tubing set or cable, locates the end that connects to the console, and aseptically transfers that end to the circulating nurse. The circulating nurse aseptically accepts the end of the tubing set or cable presented by the scrub nurse, locates the mating connector on the console, and makes the console connection. This is done for each individual tubing set or cable.

In addition to transferring the console connectors to the sterile field, the scrub nurse must assemble various components in the sterile field prior to the priming of the system. Priming consists of filling the infusion/irrigation and aspiration tubing with fluid prior to the start of surgery. Components requiring assembly consist of the ultrasonic handpiece, the posterior infusion tubing set, the airline, and the vitrectomy probe. Before priming, the posterior infusion tubing set and airline are connected to a 3-way stopcock and infusion cannula provided in the pack. Then the infusion cannula and vitrectomy probe are placed in a cup or other suitable container prior to priming. Once set-up, the system can be primed and is then ready for use.

It is typical for the console to be placed at the foot of the surgical table or to the side of the surgical table near the scrub nurse. This requires that the tubing sets or cables attached to the console must traverse the distance from the surgical site (the eye) to or near the foot of the patient. It is quite normal that the tubing sets and cables intertwine and intermingle along this distance. Another complicating factor arises from the way the tubing sets and cables are packaged. Since the tubing sets and cables are tightly coiled, they are not completely straight. This adds to the mixing and intertwining of the tubing. In addition, the fact that the surgical procedure is performed in a darkened operating room makes the management of this tubing during the surgical procedure at best difficult.

Therefore, a need exists in the ophthalmic surgical field for a kit management system that is customizable and versatile, that facilitates the scrub nurse's set-up of the consumables before use, that minimizes the number of aseptic transfers from the sterile field to the non-sterile field, that simplifies the circulating nurse's connection of the console fittings to the unit, that improves the management of the tubing and cables from the patient to the console, and that provides protection for the various instruments and tubing of the kit. Prior art surgical drapes have attempted to address these needs. For example, U.S. Pat. No. 5,464,025 discloses an ophthalmic surgical drape having pockets for surgical instruments at one end of the drape, pockets for coils of various fluid, optical, or power lines and their associated connectors at the opposite end of the drape, and fasteners for attaching the lines to the drape therebetween. However, while this surgical drape provides some improvement in console connections, in tubing management, and in customization for non-routine surgical set-ups, it does not sufficiently address the other needs discussed above. More specifically, the drape does not allow the scrub nurse to easily identify the various instruments and connectors stored in the drape's pockets and thus is less than desirable from the perspective of facilitating consumable set-up. In addition, since the line connectors are stored separately in individual pockets, the drape does not minimize the number of aseptic transfers between the scrub nurse and the circulating nurse. Finally, the drape provides minimal if no protection for the components of the kit.

SUMMARY OF THE INVENTION

One aspect of the present invention is a kit management system for use in microsurgery. The kit management system includes a plurality of tubing, an instrument tray, a connector tray, and a tubing organizer disposed between the instrument tray and the connector tray for removably receiving the plurality of tubing. Each of the tubing is coupled to a surgical instrument on a first end and a connector on a second end. The instrument tray has a plurality of cavities, each of which has a geometry for removably receiving one of the surgical instruments. The connector tray has a plurality of cavities, each of which has a geometry for removably receiving one of the plurality of connectors.

In another aspect, the present invention is a tubing organizer for removably receiving and holding a plurality of tubing in a spaced relationship during microsurgery. The tubing organizer has a base, foam coupled to a first side of the base, a cover, and a hinge rotationally coupling the base and the cover.

BRIEF DESCRIPTION OF THE DRAWINGS

For a more complete understanding of the present invention, and for further objects and advantages thereof, reference is made to the following description taken in conjunction with the accompanying drawings in which:

FIG. 8 is a top, perspective view of the tubing organizer of FIG. 7 in an open position; and FIG. 9 is a bottom, perspective view of the tubing organizer of FIG. 7 in an open position.

DETAILED DESCRIPTION OF THE PREFERRED EMBODIMENTS

The preferred embodiments of the present invention and their advantages are best understood by referring to FIGS. 1 through 9 of the drawings, like numerals being used for like and corresponding parts of the various drawings.

Figure 2:
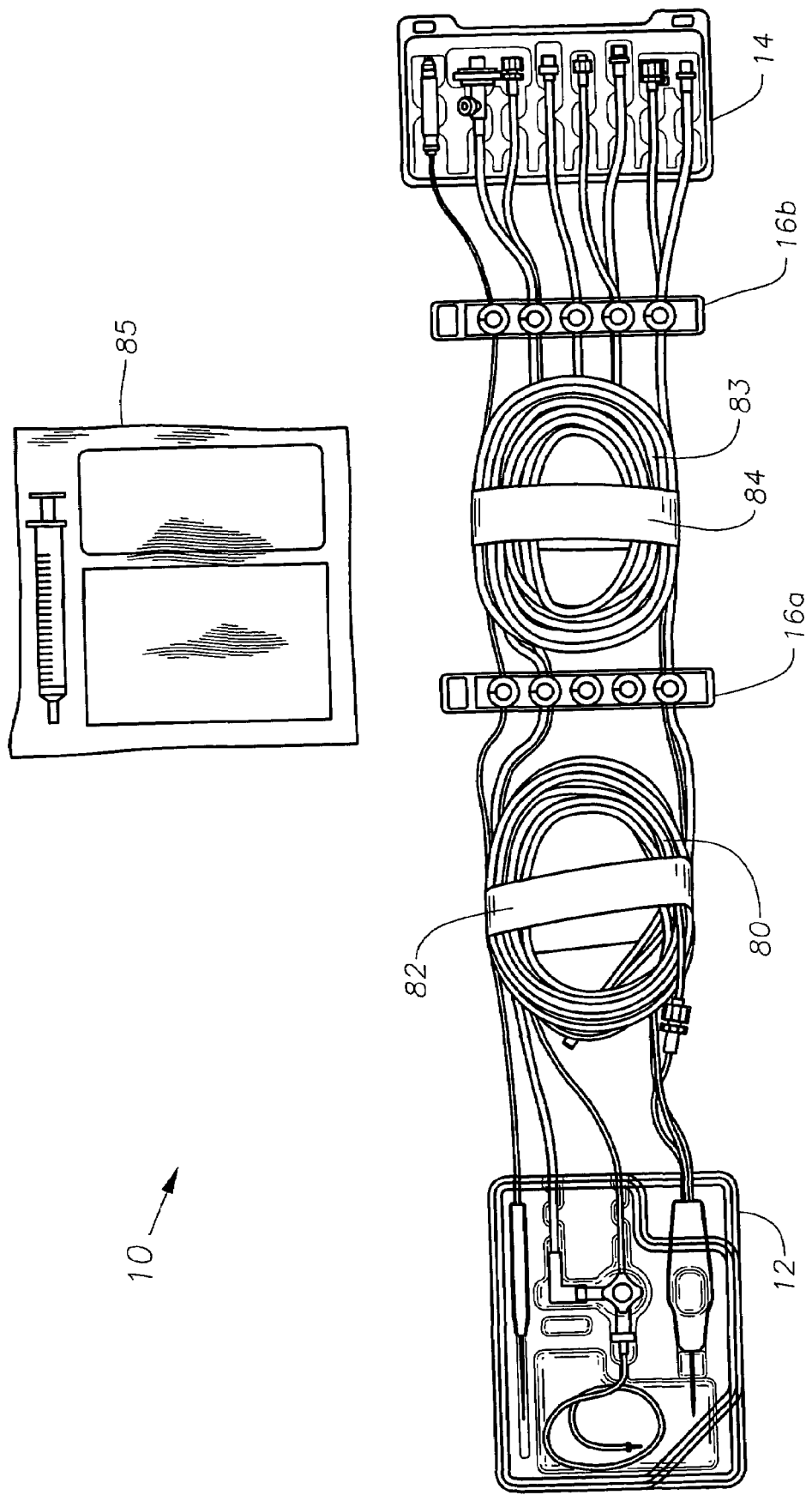
FIG. 2 is a top, perspective view of the tubing management system of FIG. 1 in a partially unfolded position.
Figure 3:
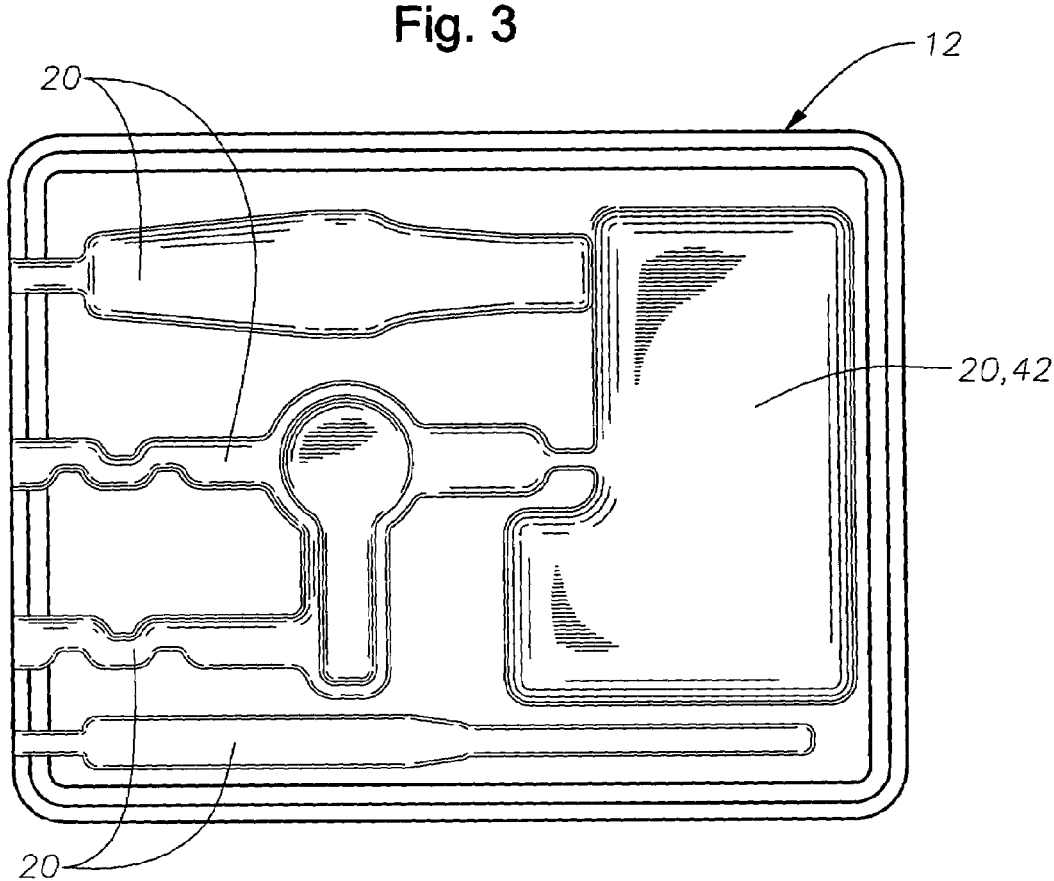
FIG. 3 is a top, perspective view of an instrument tray and cover of the tubing management system of FIG. 1.
Figure 3:
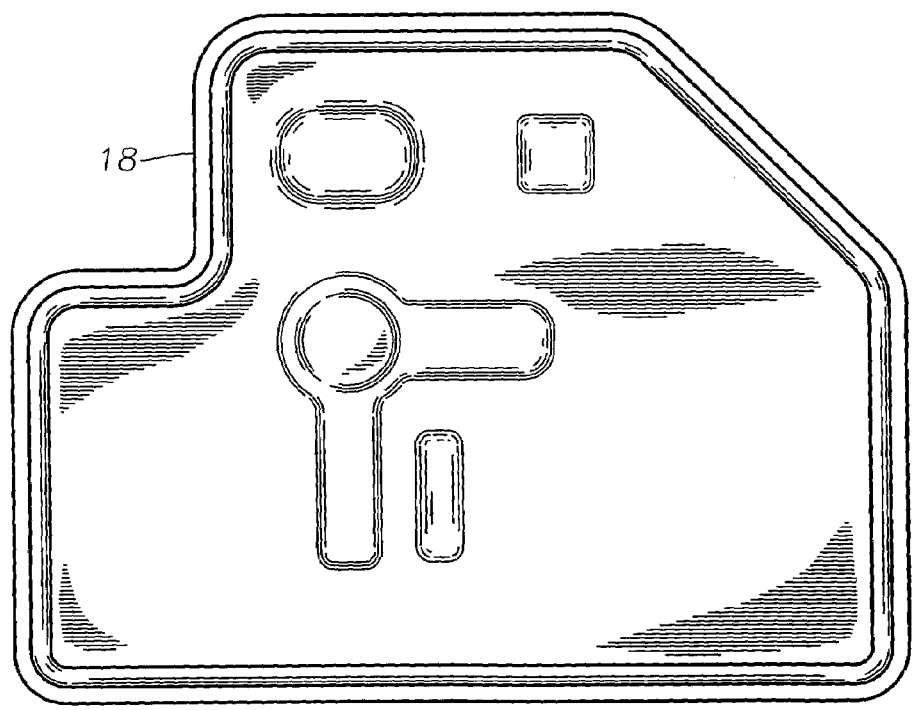
Figure 4:
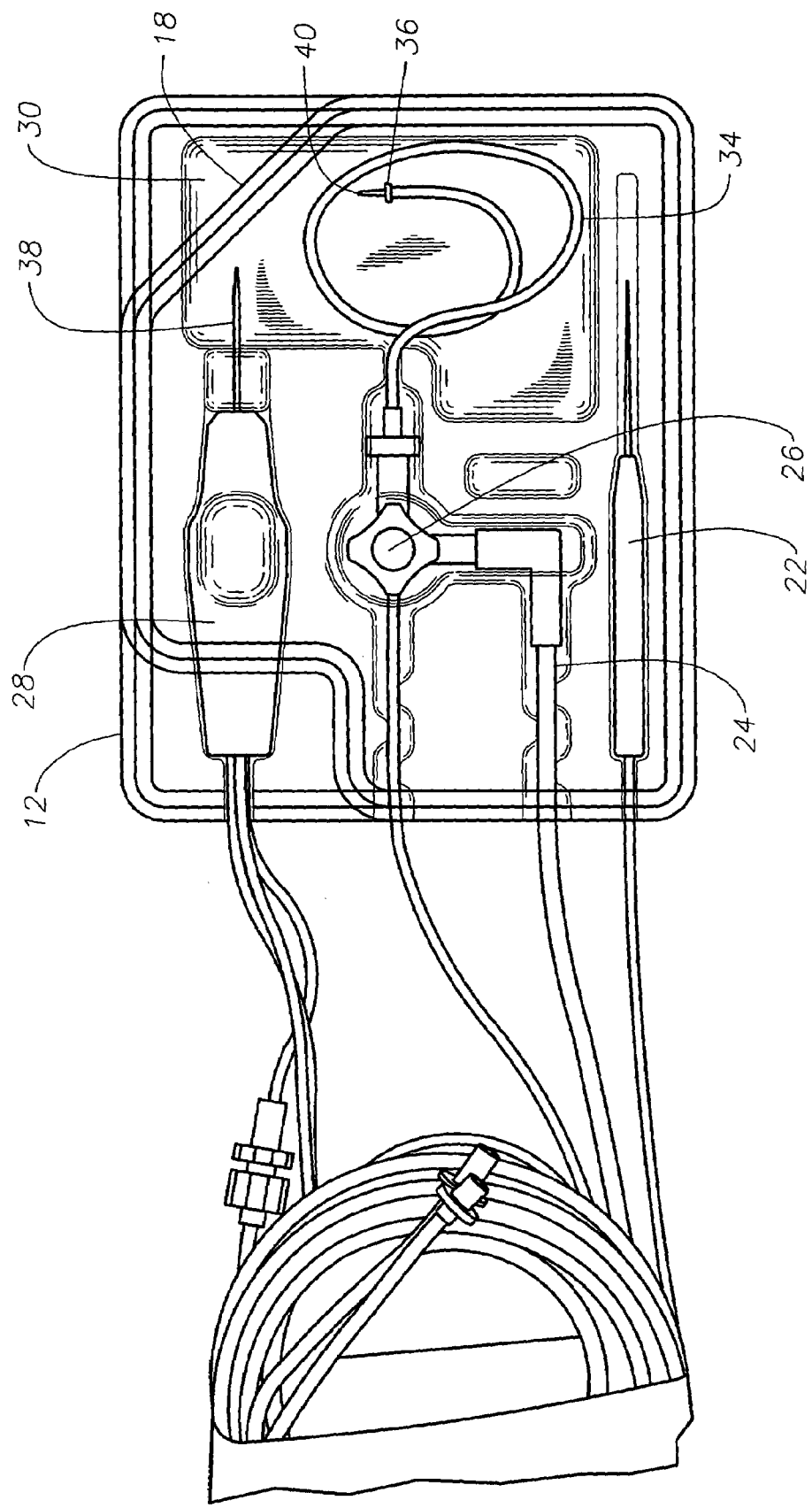
FIG. 4 is a top, perspective view of the instrument tray of FIG. 3 with surgical instruments disposed therein.
Figure 5:
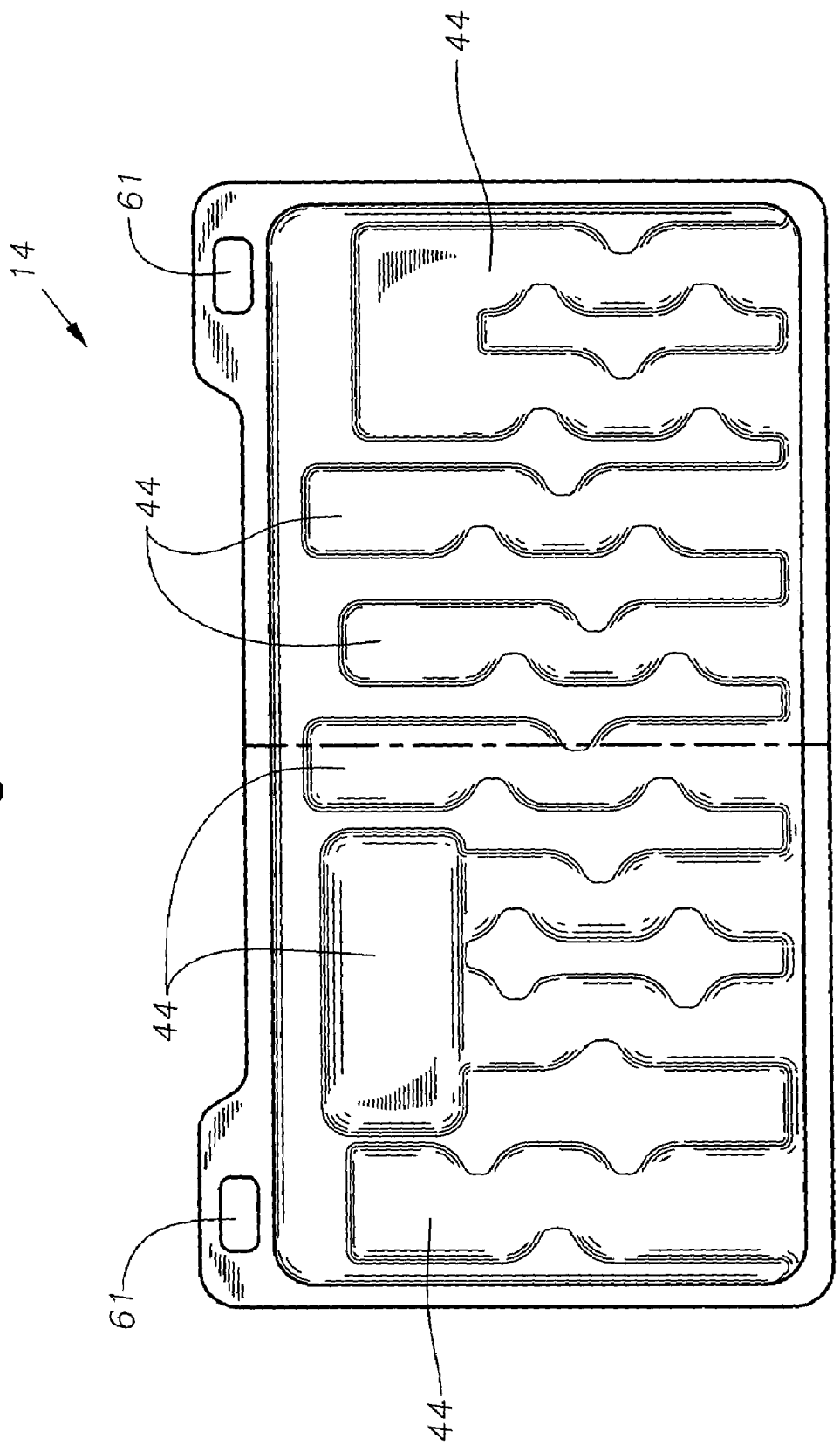
FIG. 5 is a top, perspective view of a connector tray of the tubing management system of FIG. 1.
Figure 6:
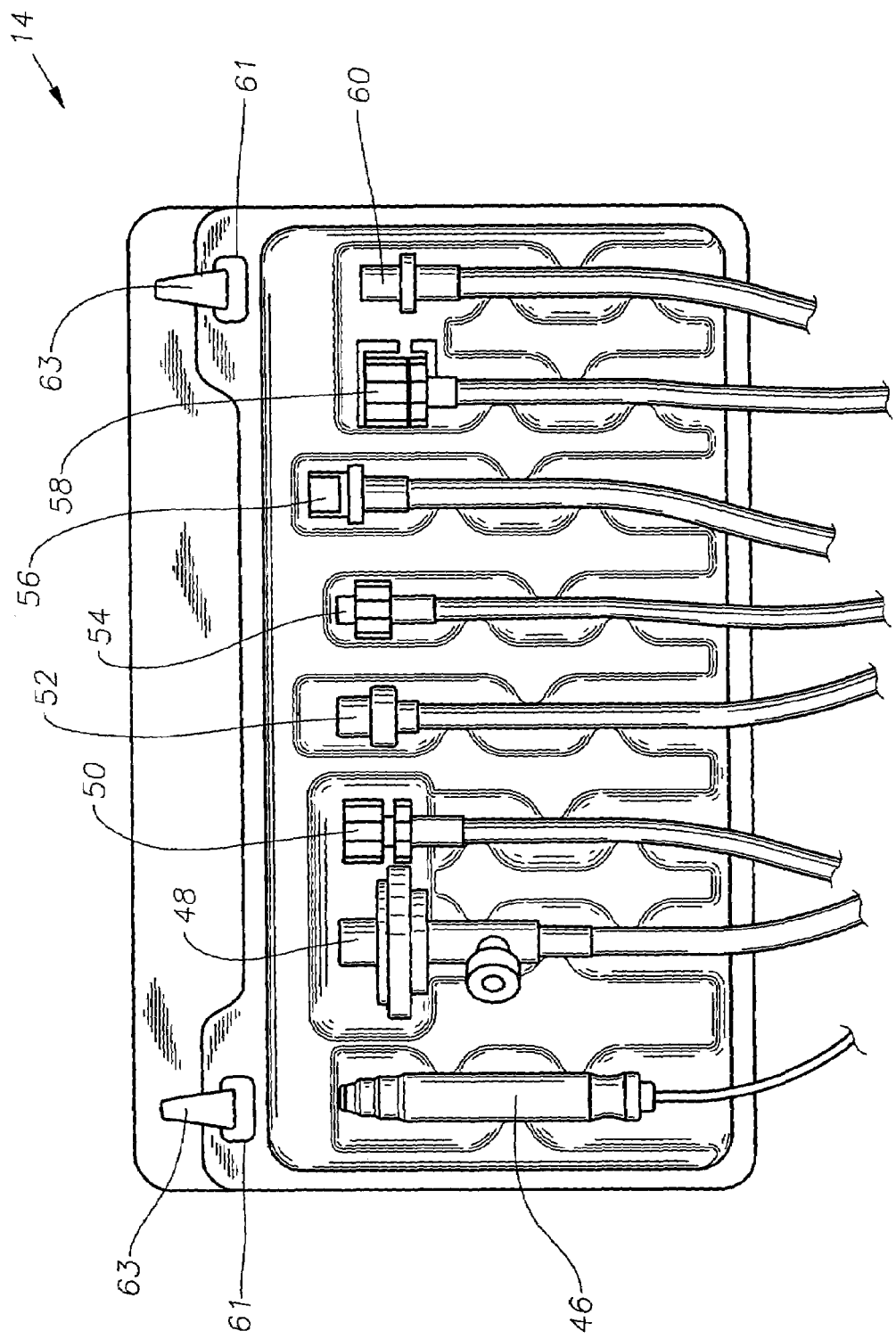
FIG. 6 is a top, perspective view of the connector tray of FIG. 5 with connectors disposed therein.

Kit management system 10 generally includes a instrument tray 12, a connector tray 14, and at least one tubing organizer 16. Kit management system 10 preferably includes two tubing organizers 16a and 16b, as is best shown in FIG. 2.

Instrument tray 12 preferably includes a cover 18. Tray 12 and cover 18 are preferably thermoformed components. Cover 18 preferably snap-fits onto tray 12. Tray 12 is formed with a plurality of cavities 20 for receiving the various surgical instruments and their associated tubing typically found in an ophthalmic surgical kit. For example, in FIG. 4 tray 12 is shown receiving a fiber optic illuminator 22, an air line 24, a stopcock 26, a vitrectomy probe 28, an infusion line 34, and an infusion cannula 36. However, instruments 22-36 may be any instruments conventionally used in microsurgery. Tray 20 may be formed with different numbers and/or geometries of cavities 20 as required. Instruments 22-36 are preassembled (e.g. infusion cannula 36, infusion line 34, stopcock 26, and air line 24) to eliminate the need for the scrub nurse to find and assemble these components in a pack. A tip 38 of vitrectomy probe 28, and a tip 40 of infusion cannula 36, are preferably disposed within a cup 42, which is one of the cavities 20 of tray 12 designed to receive and hold a surgical fluid (not shown). Cup 42 may be filled with surgical fluid via a triangular opening 30 formed by tray 12 and cover 18. This arrangement facilitates automatic priming of the aspiration line of vitrectomy probe 28 and infusion cannula 36. Tray 12 and cover 18 are preferably made from a substantially transparent plastic so that the components in cavities 20 are easily visible to the scrub nurse. This feature facilitates the set-up of the consumables before use and provides protection for instruments 22-36.

Connector tray 14 is preferably a thermoformed component and may alternatively be a die-cut folded component. Tray 14 is formed with a plurality of cavities 44 for accepting the various connectors and their associated tubing typically found in an ophthalmic surgical kit. For example, in FIG. 6 tray 14 is shown receiving a fiber optic illuminator console connector 46, an air line filter console connector 48, an infusion line console connector (with cap) 50, a vitrectomy probe pneumatic console connector 52, a vitrectomy probe aspiration console connector 54, a vitrectomy probe pneumatic console connector 56, an irrigation line console connector (with cap) 58, and an aspiration line console connector 60. However, connectors 46-60 may be any connectors conventionally used in microsurgery, such as, by way of example, luer lock, CPC, Lemo, or fiber optic connectors. Tray 14 may be formed with different numbers and/or geometries of cavities 44 as required. Tray 14 allows the scrub nurse to easily locate and aseptically transfer all of the connectors 46-60 to the circulating nurse with only one transfer. Alternatively, tray 14 allows the scrub nurse to aseptically transfer the connectors to the surgical console in the absence of the circulating nurse. The arrangement and positioning of the connectors in cavities 44 of tray 14 preferably mirror the arrangement and positioning of the mating ports on the console, which facilitates the circulating nurse's connection of the connectors to the console. Additionally, tray 14 can have symbols formed near each cavity 44 that match a corresponding symbol on the console. Furthermore, tray 14 is preferably made from a substantially transparent plastic so that the connectors 46-60 in cavities 44 are easily visible to both the scrub and circulating nurses. This feature facilitates the set-up of the consumables before use, simplifies the circulating nurse's connection of the connectors to the surgical console, and provides protection for the connectors. Tray 14 may be formed with one or more holes 61 for conveniently and removably disposing on hooks or other hanging apparatus 63 of a surgical console.

Figure 7:
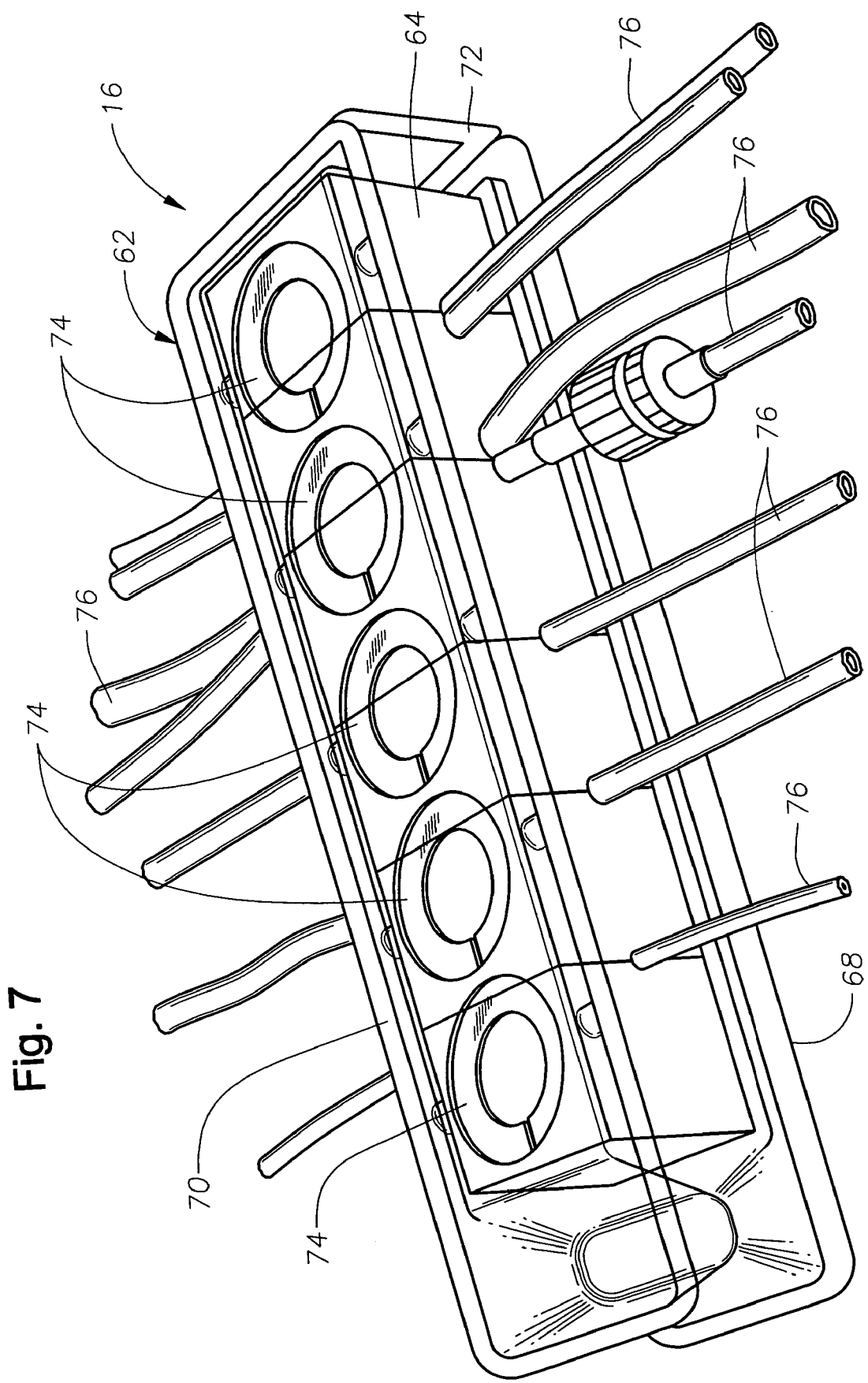
FIG. 7 is a top, perspective view of a tubing organizer of the tubing management system of FIG. 1 in a closed position.

Tubing organizer 16 is preferably a thermoformed component and may alternatively be a die-cut folded component. Tubing organizer 16 generally includes a hinged component 62, foam 64, and an adhesive strip 66. Foam 64 includes a plurality of slits 80 for removably receiving tubing 76 connecting the instruments stored in cavities 20 of tray 12 and the connectors stored in cavities 44 of tray 14. Hinged component 62 preferably includes a base 68, a cover 70, and a hinge 72 rotationally coupling base 68 and cover 70. Hinged component 62 may be moved from a closed position as shown in FIG. 7 to an open position as shown in FIGS. 8-9. In the closed position, cover 70 secures tubing 76 within slits 80 of foam 64. Adhesive strip 66 is coupled to one side of base 68, and foam 64 is coupled to an opposite side of base 68. Cover 70 preferably includes a plurality of tubing restraints 74. As shown in the Figures, tubing restraints 74 preferably are tubing loops. However, tubing restraints 74 may have other geometries for routing and holding tubing, such as, by way of example, tubing channels. Tubing restraints 74 are for removably receiving extra tubing 78 that is not part of the packaged tubing management system 10 when hinged component 62 is moved to its open position. As used herein, "tubing" refers to any variety of fluid, optical (e.g. light or laser), or power (e.g. electrical or pneumatic) tubing, cables, or lines conventionally used in microsurgery. By way of example, tubing 76 and 78 may refer to flexible fluid tubing, electric power cables, or fiber optic cables. As best shown in FIG. 2, kit management system 10 preferably includes two tubing organizers 16, a first tubing organizer 16a near tray 12 for use in the sterile field and a second tubing organizer 16b near tray 14 for use in the non-sterile field.

Figure 1:
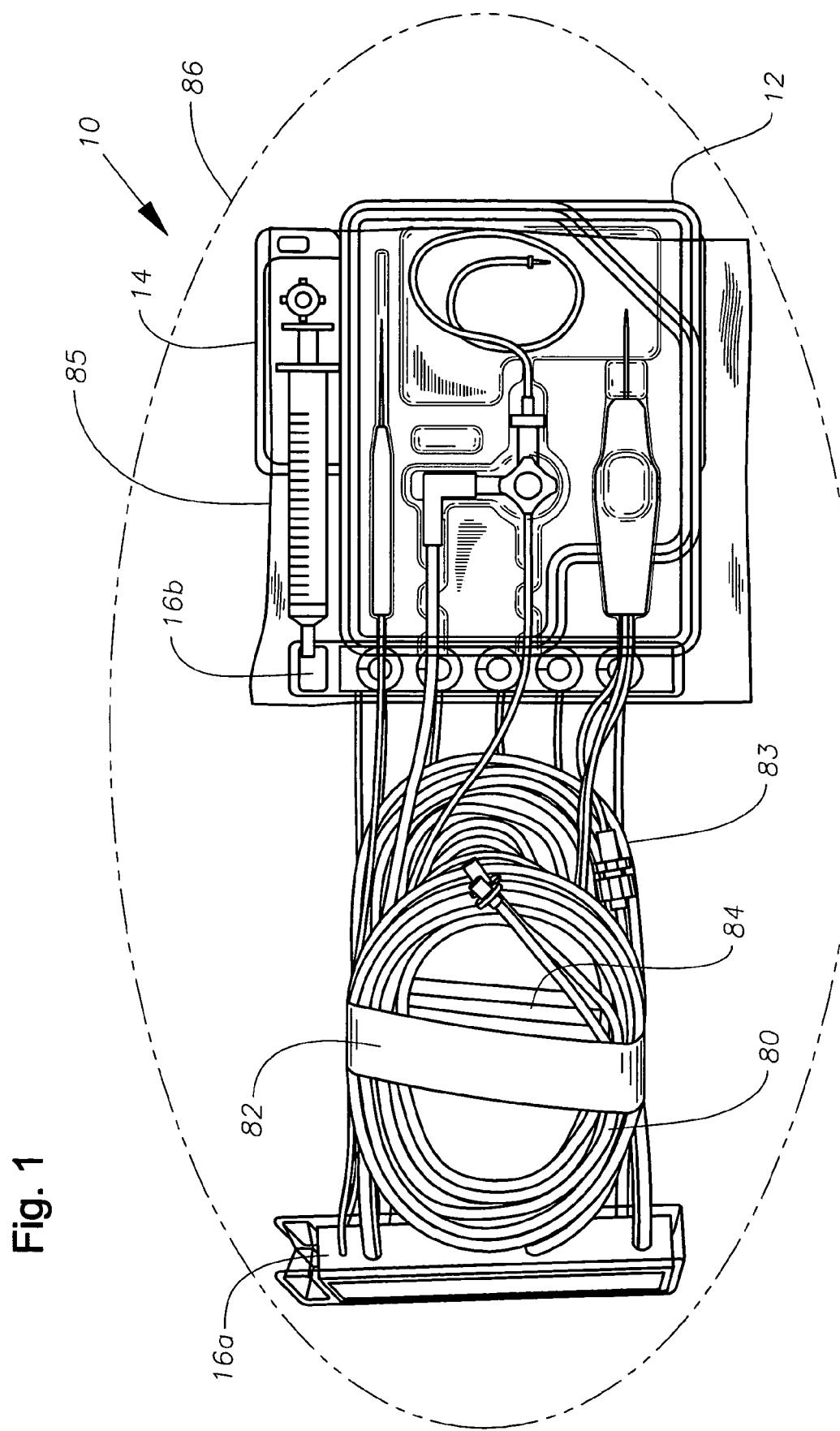
FIG. 1 is a top, perspective view of a packaged tubing management system according to a preferred embodiment of the present invention.

Kit management system 10 is preferably packaged as shown best in FIGS. 1-2. The portion of tubing 76 between tray 12 and tubing organizer 16a is coiled into a service loop 80 and secured with a paper band 82. The portion of tubing 76 between tubing organizer 16a and tubing organizer 16b and tray 14 is coiled into a service loop 83 and secured with a paper band 84. Bag 85 may contain various small items used during an ophthalmic surgical procedure, such as, by way of example, a console drape, syringe, and scleral plugs. The kit management system 10 as shown in FIG. 2 is then folded between tubing organizers 16a and 16b so as to be disposed into the position shown in FIG. 1. The folded kit management system 10 is then placed in a second plastic bag 86 (shown schematically in FIG. 1) that is sealed and sterilized.

The following describes a preferred procedure whereby nurses or other medical personnel may use kit management system 10 during ophthalmic surgery. The circulating nurse aseptically transfers a packaged kit management system 10 to the scrub nurse in the sterile field. The scrub nurse opens bag 86, removes kit management system 10, and positions the kit management system 10 within the sterile field as shown in FIG. 2. The scrub nurse then removes paper band 84, uncoils service loop 83, and aseptically transfers tubing organizer 16b, tray 14, and the portion of tubing 76 therebetween to the circulating nurse outside the sterile field.

The circulating nurse removes the paper backing from adhesive strip 66 of tubing organizer 16b and secures tubing organizer 16b in the non-sterile field. The circulating nurse hangs tray 14 on hooks or other hanging apparatus 63 on the surgical console via holes 61. The circulating nurse may quickly and visually check to see that all of the necessary connectors 46-60 are within tray 14. The circulating nurse then connects each of connectors 46-60 to its corresponding port on the surgical console and proceeds to other duties.

The scrub nurse removes the paper backing from adhesive strip 66 of tubing organizer 16a and secures tubing organizer 16a within the sterile field, such as, by way of example, on the surgical drape covering the patient or on the Mayo tray stand. The scrub nurse removes paper band 82 from service loop 80. The scrub nurse may quickly and visually check to see that all of the necessary instruments 22-36 are within tray 12. The scrub nurse removes cover 18 from tray 12 and fills cup 42 with a surgical fluid for priming vitrectomy probe 28, infusion tubing 34, and infusion cannula 36. Alternatively, the scrub nurse may elect to keep cover 18 disposed on tray 12 and fill cup 42 with surgical fluid via triangular opening 30. If desired, the scrub nurse may open cover 70 of tubing organizer 16a and use tubing restraints 74 to secure tubing 78. The system may be primed and is then ready for use.

From the above, it may be appreciated that the present invention provides improved apparatus and methods for managing and handling the various components of an ophthalmic surgical kit. The kit management system is easy for nurses and other medical personnel to use and may be made in an economical manner. The kit management system maximizes both patient safety as well as the success of the surgical procedure.

The present invention is illustrated herein by example, and various modifications may be made by a person of ordinary skill in the art. For example, although the kit management system is described above as a kit management system for ophthalmic surgery, it is also applicable to other microsurgeries, such as, by way of example, and otic surgeries or nasal surgeries.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A kit management system for use in microsurgery, comprising:
   a plurality of tubing, each of said tubing coupled to a surgical instrument on a first end and a connector on a second end;
   an instrument tray having a plurality of cavities disposed thereon and a removable cover, each of said cavities removably receiving one of said surgical instruments;
   a connector tray having a plurality of cavities disposed thereon, each of said cavities removably receiving one of said connectors; and
   a tubing organizer disposed between said instrument tray and said connector tray for removably securing and separating said plurality of tubing.

2. The kit management system of claim 1 wherein said instrument tray is formed of a transparent plastic.

3. The kit management system of claim 1 wherein said connector tray is formed of a transparent plastic.

4. The kit management system of claim 1 wherein said instrument tray includes a cup for receiving surgical fluid for priming one of said surgical instruments.

5. The kit management system of claim 1 wherein said connector tray includes a hole for removably disposing said connector tray on a hanging apparatus of a surgical console.

6. The kit management system of claim 1 wherein said tubing organizer comprises a base, foam coupled to a first side of said base, a cover, and a hinge rotationally coupling said base and said cover.

7. The kit management system of claim 6 wherein said tubing organizer further comprises an adhesive strip coupled to a second side of said base opposite said first side.

8. The kit management system of claim 6 wherein said foam comprises a plurality of slits, each of said slits for removably securing and separating each of said plurality of tubing.

9. The kit management system of claim 6 wherein said cover comprises a tubing restraint having a generally ring-shaped geometry.

10. The kit management system of claim 1 further comprising a second tubing organizer disposed between said instrument tray and said connector tray.

11. The kit management system of claim 10 wherein said first tubing organizer is disposed proximate said instrument tray for positioning in a sterile field, and said second tubing organizer is disposed proximate said connector tray for positioning in a non-sterile field.

12. The kit management system of claim 1 wherein said kit management system is for use in an ophthalmic, otic, or nasal surgery.

* * * * *